(12) United States Patent
Kluge et al.

(10) Patent No.: US 8,668,663 B2
(45) Date of Patent: Mar. 11, 2014

(54) DEVICE FOR THE REPEATED PIERCING OF A SKIN WITH A HAND-HELD DEVICE, A NEEDLE MODULE AND A METHOD FOR ASSEMBLING THE HAND-HELD DEVICE

(75) Inventors: Jörn Kluge, Teltow (DE); Kristian Plückhahn, Berlin (DE); Denis Podolski, Berlin (DE); Ryanto Chandra Halim, Berlin (DE)

(73) Assignee: Mt. Derm GmbH, Berlin (DE)

( * ) Notice: Subject to any disclaimer, the term of this patent is extended or adjusted under 35 U.S.C. 154(b) by 1588 days.

(21) Appl. No.: 11/819,692

(22) Filed: Jun. 28, 2007

(65) Prior Publication Data

US 2008/0077170 A1    Mar. 27, 2008

(30) Foreign Application Priority Data

Jun. 28, 2006 (EP) .................................. 06013344

(51) Int. Cl.
*A61B 17/20* (2006.01)
(52) U.S. Cl.
USPC .............................................. 604/22; 604/46
(58) Field of Classification Search
USPC ........................................ 604/22, 156, 187
See application file for complete search history.

(56) References Cited

U.S. PATENT DOCUMENTS

| 4,820,962 | A | 4/1989 | Millauer |
| 6,086,598 | A * | 7/2000 | Appelbaum et al. .......... 606/107 |
| 6,345,553 | B1 | 2/2002 | Adler et al. |
| 6,505,530 | B2 | 1/2003 | Adler et al. |
| 6,908,472 | B2 * | 6/2005 | Wiener et al. ................. 606/169 |
| 2001/0010026 | A1 | 7/2001 | Desmoulins |
| 2001/0052416 | A1 | 12/2001 | Wissmach et al. |
| 2004/0220602 | A1 | 11/2004 | Deng et al. |
| 2006/0129140 | A1 | 6/2006 | Todd et al. |
| 2007/0016185 | A1 * | 1/2007 | Tullis et al. .................... 606/41 |

FOREIGN PATENT DOCUMENTS

| DE | 299 19 199 U | 1/2000 |
| DE | 29923931 U1 | 7/2001 |
| DE | 10118034 A1 | 10/2002 |
| EP | 0269562 A2 | 6/1988 |
| EP | 1118919 A1 | 7/2001 |
| EP | 1163974 A1 | 12/2001 |
| FR | 2023246 A | 8/1970 |
| WO | 2005-110303 A1 | 11/2005 |

* cited by examiner

*Primary Examiner* — Nicholas Lucchesi
*Assistant Examiner* — Melissa A Snyder
(74) *Attorney, Agent, or Firm* — Smith Patent Office (57) ABSTRACT

The invention relates to a device for the repeated piercing of a skin, with a hand-held device (1), which has a drive module (2) with a drive unit (4) that is configured for the purpose of producing a driving force, and a needle module (3) in which a piercing apparatus (6) is moveably located in the longitudinal direction of the needle module (3) and which is detachably coupled to the drive module (2) in such a way that the driving force is conducted into the piercing apparatus (6), wherein the needle module (3) has identification means (14) which can be evaluated with an evaluation apparatus (13) allocated to the identification means (14) and enclosed by the drive module (2). Furthermore, the invention relates to a needle module as well as a method for assembling the hand-held device.

25 Claims, 10 Drawing Sheets

DEVICE FOR THE REPEATED PIERCING OF A SKIN WITH A HAND-HELD DEVICE, A NEEDLE MODULE AND A METHOD FOR ASSEMBLING THE HAND-HELD DEVICE

The invention relates to a device for the repeated piercing of a skin with a hand-held device which has a drive module with a drive unit and a needle module, as well as a needle module for such a device and a method for assembling the hand-held device.

BACKGROUND OF THE INVENTION

Devices for the repeated piercing of a skin with a hand-held device which has a drive module with a drive unit, that is configured for the purpose of producing a driving force, and a needle module in which a piercing apparatus is moveably located in the longitudinal direction of the needle module and which is detachably coupled to the drive module in such a way that the driving force is conducted into the piercing apparatus are used in various applications for the purpose of piercing a skin for the injection of an active ingredient into the skin. The piercing apparatus performs thrust and retraction movements with the support of the driving force. The active ingredient applied here can be for example a colouring material, a cosmetic active ingredient or a medical active ingredient. In combination with the colouring material, the hand-held device is used, for example, as a tattoo and permanent make-up hand-held device. For the medical application, vaccines or other medical active ingredients can be injected into the skin with the hand-held device.

From the document DE 299 19 199, and with such devices for the repeated piercing of a skin, it is known to envisage a modular configuration in such a way that the hand-held device is formed with a drive module and a needle module to be detachably secured to this drive module. In order to ensure a correct usage of the hand-held device, it is particularly significant that the drive module which disposes of the drive apparatus, an electric motor for example, is coupled to the right needle module.

SUMMARY OF THE INVENTION

Therefore, the object of the invention is to provide an improved device for the repeated piercing of a skin with a hand-held device, an improved needle module for the device and an improved method for the assembling of the hand-held device which ensure an orderly usage of drive module and needle module.

This object is solved according to the invention by a device for the repeated piercing of a skin according to the independent Claim 1, a needle module for the device according to the independent Claim 19 as well as a method for the assembling of the hand-held device according to the independent Claim 20 Advantageous embodiments of the invention are subject-matter of dependent claims.

The invention comprises the concept of envisaging a device for the repeated piercing of a skin wherein a hand-held device which has a drive module with a drive unit, that is configured for the purpose of producing a driving force, and a needle module in which a piercing apparatus is moveably located in the longitudinal direction of the needle module and which is detachably coupled to the drive module in such a way that the driving force is conducted into the piercing apparatus, and an identification means or mechanism is envisaged which can be evaluated with an evaluation apparatus allocated to the identification means or mechanism and enclosed by the drive module. In this way, random identification information can be given to the needle module during the manufacturing process, and this information can be evaluated within the framework of usage of the needle module in conjunction with the drive module. Depending on the case of application, the needle module can be individually configured with the support of the identification means or mechanism. The adherence to safety regulations is facilitated and ensured in this way. In addition and with the invention, it is easier and possible to prevent inappropriate use of the needle module.

A preferred further development of the invention envisages that the identification means or mechanism can be evaluated by the evaluation apparatus with the support of at least one of the following evaluation methods: wireless data transmission such as radio data transmission, infrared data transmission and bluetooth data transmission, inductive evaluation, capacitive evaluation, optical evaluation and mechanical evaluation. The advantage of a mechanical evaluation is the uncomplicated configuration. For example a recess can be envisaged on the drive module which, with regard to its shape, is essentially adapted to a projection at the needle module so that only one needle module with such a specific projection can be coupled with the appropriate drive module. The projection on the needle module forms the identification means or mechanism which is evaluated by the allocated recess (evaluation apparatus) at the drive module. The configuration options with regard to the evaluation of the identification means or mechanism is, however, particularly manifold with the use of a data transmission.

A preferred embodiment of the invention can envisage that the evaluation apparatus has a transmission device and a detection device which is configured for the purpose of detecting signals sent from the transmission device. For example, the signals interact with the identification means or mechanism and the signals change as a result. The changed signals are then detected by the detection device.

Furthermore, and with a further embodiment according to the invention, it can be envisaged that the identification means or mechanism comprises a masking means or mechanism which is configured and mask the signals sent from the transmission device. The masked signals are then detected by the detection device. An evaluation of the identification means or mechanism takes place in this way.

The masking means or mechanism advantageously comprises a mask which is configured in order to mask the signals sent from the transmission device according to a code allocated to the needle module. In one embodiment the mask is formed as a hollow cylinder with recesses, for example as a perforated orifice or as a perforated mask. The result obtained in this way is that the signals on the signal path to the detection device are partially blocked, through which a modulation of the signals is achieved, wherein the modulation depends particularly on the number and/or the location of the recesses or the diameter of the holes in the perforated orifice. It can also be envisaged to locate the transmission device at one surface of the drive module facing the needle module, for example essentially in a central position on the surface of the drive module facing the needle module.

It can be further envisaged that the mask has signal conducting means or mechanism, which is configured, in order to transmit the signals from the transmission device to the detection device. For example, the signal conducting means or mechanism can have reflecting elements which reflect the signals. It can be particularly envisaged that a slanted reflecting surface is formed on the needle module which reflects the signals to the detection device. The detection device is preferably arranged at a projection. If the needle module is coupled to the drive module, the slanted surface reflects the signals sent from the transmission device to the detection device. For example, and depending on an angle of the slanted surface with reference to a longitudinal axis of the needle module, the signals are reflected to various areas of the detection device. However, it can also be envisaged to arrange the slanted surface at different positions at the needle module. In this way a recognition of different types of needle modules is made possible in that various areas, to which the signals at the detection device are reflected, have different types of needle modules allocated.

In one further development, several reflecting elements are arranged adjacent to one another on the needle module. It can be envisaged in one embodiment that a non-reflecting area is formed between two reflecting elements. The arrangement of reflecting elements and/or non-reflecting areas therefore form a recognition zone. In particular, the transmission device and the detection device can be formed on a carrier component, wherein the carrier component is arranged in such a way that it extends over the drive module in the direction of the needle module at the drive module, so that the carrier component is located opposite the recognition zone when the drive module and the needle module are coupled with one another. During the coupling connection of the needle module with the drive module, the carrier component therefore sweeps over the recognition zone. The signals sent from the transmission device are correspondingly reflected by the recognition zone, wherein the reflecting signals are detected by the detection device. In particular, a recognition of the needle module can then be achieved in such a way that the number of detected signals depend, for example, on a number of the reflecting elements.

It can be envisaged in another embodiment to form a reference area on the needle module, wherein the reference area in one embodiment comprises reflecting elements arranged adjacent to one another. In particular, the reference area cannot also have reflecting areas which, for example, are arranged between two reflecting elements. Preferably, a reference code is allocated to the arrangement of reflecting elements and/or of non-reflecting areas. The carrier component can be particularly formed in such a way that, if the drive module is coupled with the needle module, the carrier component lies opposite the recognition zone as well as the reference area. During the coupling-connection of the needle module with the drive module, the carrier component sweeps over the recognition zone and the reference area. The detection device detects the signals reflected by the recognition zone and the reference area wherein the signals reflected by the reference area, for example, form a reference for the signals reflected by the recognition zone.

It can be further envisaged that the transmission device is formed with at least one light source that discharges optical signals, for example a light-emitting diode, an organic light-emitting diode, an inorganic light-emitting diode, a polymer light-emitting diode, a hybrid light-emitting diode or a laser. In one embodiment the detection device comprises at least one photo diode. In particular, the light source is formed in such a way that the light source discharges diffuse light.

With a purposeful embodiment of the invention, it can be envisaged that the identification means or mechanism has an electronic identification means or mechanism with data stored therein and which can be evaluated by the evaluation apparatus. The use of the electronic identification means or mechanism has the advantage that the data stored therein can be processed in a manifold way during the evaluation. For example, control data for the operation of a hand-held device can be derived.

An advantageous embodiment of the invention envisages that the evaluation apparatus comprises a communication module allocated to the electronic identification means or mechanism, with which the stored data can be read out of the electronic identification means or mechanism and further data can be selectively stored in the electronic identification means or mechanism. The communication module is, for example, a transmission-receiver unit that is suitable for the electronic identification means or mechanism so that electronic data can be exchanged in this way.

A preferred further development of the invention envisages that the electronic identification means or mechanism comprises an RFID-chip (RFID=radio frequency identification). The RFID technology is known as such and enables a situation where random information is stored on the RFID-chip which can be read out with an allocated evaluation module.

A preferred further development of the invention envisages that the evaluation apparatus is configured for the purpose of automatically evaluating the identification means or mechanism when the needle module is coupled to the drive module.

With a purposeful embodiment of the invention, it can be envisaged that the identification means or mechanism is formed to supply at least one of the following information items that can be evaluated by the evaluation apparatus and that can be allocated to the needle module: serial number, for the drive module usable for the needle module, usage duration of the needle module, type of piercing apparatus and allowed operating parameters such as piercing frequency and operating modes.

An advantageous embodiment of the invention envisages that a control device is formed and is configured for the purpose of controlling an operation of the hand-held device.

A preferred further development of the invention envisages that the control device is implemented in at least one of the following equipment components: a hand-held device and a control unit coupled to the hand-held device. The control unit in combination with hand-held devices for skin piercing is usually used for regulating operating parameters and for providing voltage supply. The control unit itself frequently has a display unit, input means or mechanism such as rotary buttons or key panels.

A preferred further development of the invention envisages that the evaluation apparatus or selectively the control device are configured in order to block the operation of the hand-held device if it is discovered during the evaluation of the identification means or mechanism that the needle module does not have an official permit for usage with the drive module. If it is discovered during the evaluation of the identification means or mechanism that the needle module is not officially permitted for a usage with the drive module, for example on the basis of the evaluated serial number, the evaluation apparatus or selectively the control device prevent a usage of the hand-held device which is achieved in such a way, for example, that a voltage supply of the drive unit is interrupted.

With a purposeful embodiment of the invention it can be envisaged that the evaluation apparatus or selectively the control device are configured to control the operation of the hand-held device corresponding to at least one information item that can be evaluated by the evaluation apparatus and that can be allocated to the needle module.

An advantageous embodiment of the invention envisages that the hand-held device is executed as one of the following hand-held devices: permanent make-up and tattoo hand-held device, hand-held device for discharging active ingredients, and skin vaccination hand-held device.

A preferred further development of the invention envisages that the needle module is a sterilised disposable needle module. Independent of the execution as a disposable module, the needle module can be designed in such a way that it can be assembled to the drive module, or is detachable from this, as a comprehensive module in the form of individual elements, for example as a casing and needle or as a needle system.

Advantageous embodiments of the method according to the invention are described as follows in greater detail.

A preferred further development of the invention envisages that the identification means or mechanism is evaluated by the evaluation apparatus with the support of at least one of the following evaluation methods: wireless data transmission such as radio data transmission, infrared data transmission and bluetooth data transmission, inductive evaluation, capacitive evaluation, optical evaluation and mechanical evaluation.

An advantageous further development of the invention envisages that the evaluation apparatus has a transmission device and a detection device with which signals sent from the transmission device are detected.

Another purposeful embodiment of the invention envisages that the signals sent from the transmission device are masked by the masking means or mechanism comprised by the identification means or mechanism.

It can be furthermore and preferably envisaged that the masking means or mechanism comprises a mask with which the signals sent from the transmission device are masked according to a code allocated to the needle module.

A preferred further development of the invention envisages that the mask has a signal conducting means or mechanism with which the signals discharged from the transmission device are sent to the detection device.

A further purposeful embodiment of the invention envisages that the signals sent from the transmission device are discharged as optical signals from at least one light source which is comprised by the transmission device.

It can be envisaged with a purposeful embodiment of the invention that the identification means or mechanism has an electronic identification means or mechanism with data stored therein which are evaluated by the evaluation apparatus.

An advantageous embodiment of the invention envisages that the evaluation apparatus comprises a communication module allocated to the electronic identification means or mechanism with which, during the evaluation of the electronic identification means or mechanism, the stored data are read out at least partially from the electronic identification means or mechanism and, selectively, further data are stored in the electronic identification means or mechanism. Subsequently, in one embodiment it can be envisaged that information on a performed usage of the needle module is written into the identification means or mechanism, for example by the placement of a digital parameter. In this way, for example, the attempt to perform a repeated use of a needle module, which might then be already contaminated, is prevented when the electronic identification means or mechanism is read out upon a repeated coupling-connection of the needle module that during evaluation of the electronic identification means or mechanism, data from an RFID-chip comprised by the electronic identification means or mechanism are evaluated.

A preferred further development of the invention envisages that the evaluation apparatus automatically evaluates the identification means or mechanism if the needle module is coupled to the drive module.

With a purposeful embodiment of the invention it can be envisaged that the identification means or mechanism supplies at least one of the following information items that can be evaluated by the evaluation apparatus and that can be allocated to the needle module: serial number, for the needle module usable drive module, usage duration of the needle module, type of piercing apparatus and allowed operating parameters such as piercing frequency and operating modes. As a piercing apparatus, single needles or needle systems with several needles are usable.

An advantageous embodiment of the invention envisages that the operation of the hand-held device is blocked by the evaluation apparatus or selectively the control device if, during the evaluation of the identification means or mechanism, it is discovered that the needle module is not officially permitted for usage with the drive module.

A preferred further development of the invention envisages that the evaluation apparatus or selectively the control device correspondingly controls the operation of the hand-held device according to at least one information item that can be evaluated by the evaluation apparatus and that can be allocated to the needle module. A control according to the evaluation-capable information means or mechanism, for example, a restriction of the operation of the hand-held device to pre-specified operating modes which are characterised for example by a certain repeating frequency (piercing frequency) or a frequency range for the piercing apparatus or a piercing depth, namely parameters which can be adjustably set for the operation of the hand-held device by the user, preferably by the control unit.

A DESCRIPTION OF PREFERRED EMBODIMENT EXAMPLES OF THE INVENTION

The invention is described as follows in greater detail on the basis of preferred embodiment examples with reference to figures of a drawing. The figures show the following:

FIG. 3b schematically, an enlarged partial view of the hand-held device from FIG. 3a;

Figure 1:
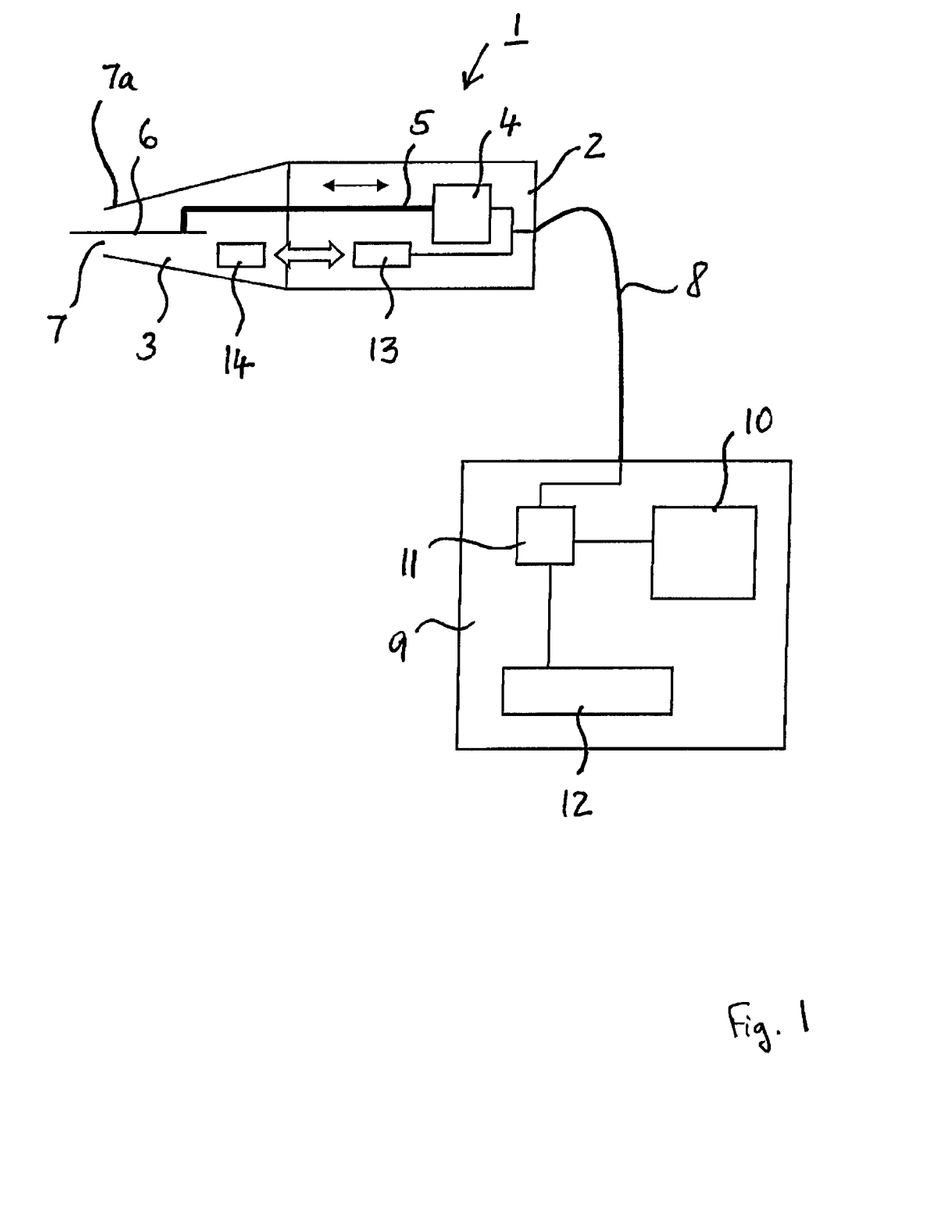
FIG. 1 schematically, a device for the repeated piercing of a skin.

FIG. 1 shows schematically an arrangement with a hand-held device 1 for the repeated piercing of a skin. The hand-held device 1 comprises a drive module 2 as well as a needle module 3 that is detachably coupled to this. In the drive module 2, an electric motor 4 is envisaged as a drive unit that couples to a needle 6 by way of a coupling mechanism 5 which itself preferably comprises a wobble disk mechanism. The needle 6 forms a piercing apparatus for skin piercing which, in other embodiments, is also formed by a system with several needles. With the support of the electric motor 4 and the coupling mechanism 5, a repeating drive movement is produced which is conducted onto the needle 6 by way of the coupling mechanism 5, so that the needle 6 is moved forwards and backwards through an opening 7 of the needle module 3. Normally, the needle 6 is coupled to the coupling mechanism 5 by a needle shaft (not shown). A needle nozzle is formed with casing sections 7a of the needle module 3 adjacent to the opening 7.

The needle module 3 is detachably connected to the drive module 2, for example by a threaded connection, an insert connection or a clamping connection. In this way it is enabled that the needle module 3, preferably executed as a disposable module, can be detached after use from the drive module 2 and then replaced. In this case, the needle module 3 is executed in such a way that it can be detached as a comprehensive module from the drive module 2. The needle module 3 is made available preferably as a suitably packed sterilised component.

The hand-held device 1 is connected to a control unit 9 by way of a connecting cable 8. With the support of the connecting cable 8, the electric motor 4 is connected in particular to a voltage supply (not shown). In addition, the connecting cable 8 in the illustrated embodiment comprises one or several cables for the transmission of electronic data. In alternative embodiments the hand-held device 1 can also be connected to the control unit 9 by way of a wireless data connection. A voltage supply of the hand-held device 1 can be executed in one embodiment with the support of a rechargeable battery integrated in the hand-held device 1.

In the control unit 9, a display unit 10, a control device 11 and an operating unit 12 are formed. Further components or assembly groups can be envisaged in the control unit 9, but are left out here for the purpose of simplified illustration. With the support of the operating unit 12, a user can enter pre-specified data for the operation of the hand-held device 1, for example by way of a key panel or with the support of rotary buttons. By way of the display unit 11, information on the operation of the hand-held device 1 are shown, for example an applied operating mode, a selected piercing frequency or similar. The display of information concerning the currently used needle module 3 can also be envisaged. The control unit 10 serves in particular the purpose of controlling the operation of the hand-held device 1, but also serves the purpose of coordinating the display indication on the display unit 11.

According to the schematic illustration in FIG. 1 an evaluation apparatus 13 is formed in the drive module 2, and this evaluation apparatus is used for the purpose of evaluating identification means or mechanism 14 at the needle module 3. The identification means or mechanism 14 and the evaluation apparatus 13 can be coupled together by mechanical, optical, capacitive or inductive means or mechanism. When coupling the needle module 3 the identification means or mechanism 14, initiated automatically or by the user, for example by a key, are evaluated by the evaluation apparatus 13. From the evaluation apparatus 13, and with the embodiment as shown, data signals are then transmitted to the control device 10 which show information which the evaluation apparatus 13 has derived from the identification means or mechanism 14. This can be, for example, a data signal showing that the needle module 3 matches the drive module 2. Such a signal, for example, can be produced by a key switch attached to the drive module 2 which is used if the needle module 3 is coupled to the drive module 2 where, for example, a projection (not shown) on the needle module 3 is pressed onto the key switch during the coupling action, wherein said key switch is integrated in the evaluation apparatus 13.

Preferred embodiments envisage, either in an alternative or supplementary mode, that the identification means or mechanism 14 comprises an electronic storage medium such as for example an RFID-chip where electronic data are stored which, on their part, can be evaluated at least partially with the support of the evaluation apparatus 13.

Depending on the data signals received from the evaluation apparatus 13, the control device 10 then controls the operation of the hand-held device 1. For example, the operation of the hand-held device 1 can be released or blocked depending on whether the data signals indicate the coupling of a correct needle module or a needle module that is not officially permitted with the drive module 2. Furthermore, the information made available by the identification means or mechanism 14 can comprise allowable operating modes of the needle module 3 or usage restrictions of the needle module 3, for example with reference to a usage duration. The control device 10 is configured in order to take into consideration the data signals sent from the evaluation apparatus 13 accordingly during the control of the operation of the hand-held device 1.

As an alternative to the embodiment in FIG. 1, the control device 10 can be at least partially integrated in the hand-held device 1, for example in the evaluation apparatus 13. For this purpose, for example a microprocessor (not shown) is integrated in the hand-held device 1, namely in the drive module 2. The usage of the information derived from the identification means or mechanism 14 for the control of the hand-held device 1 can then at least partially take place in the hand-held device 1 itself.

Figure 2:
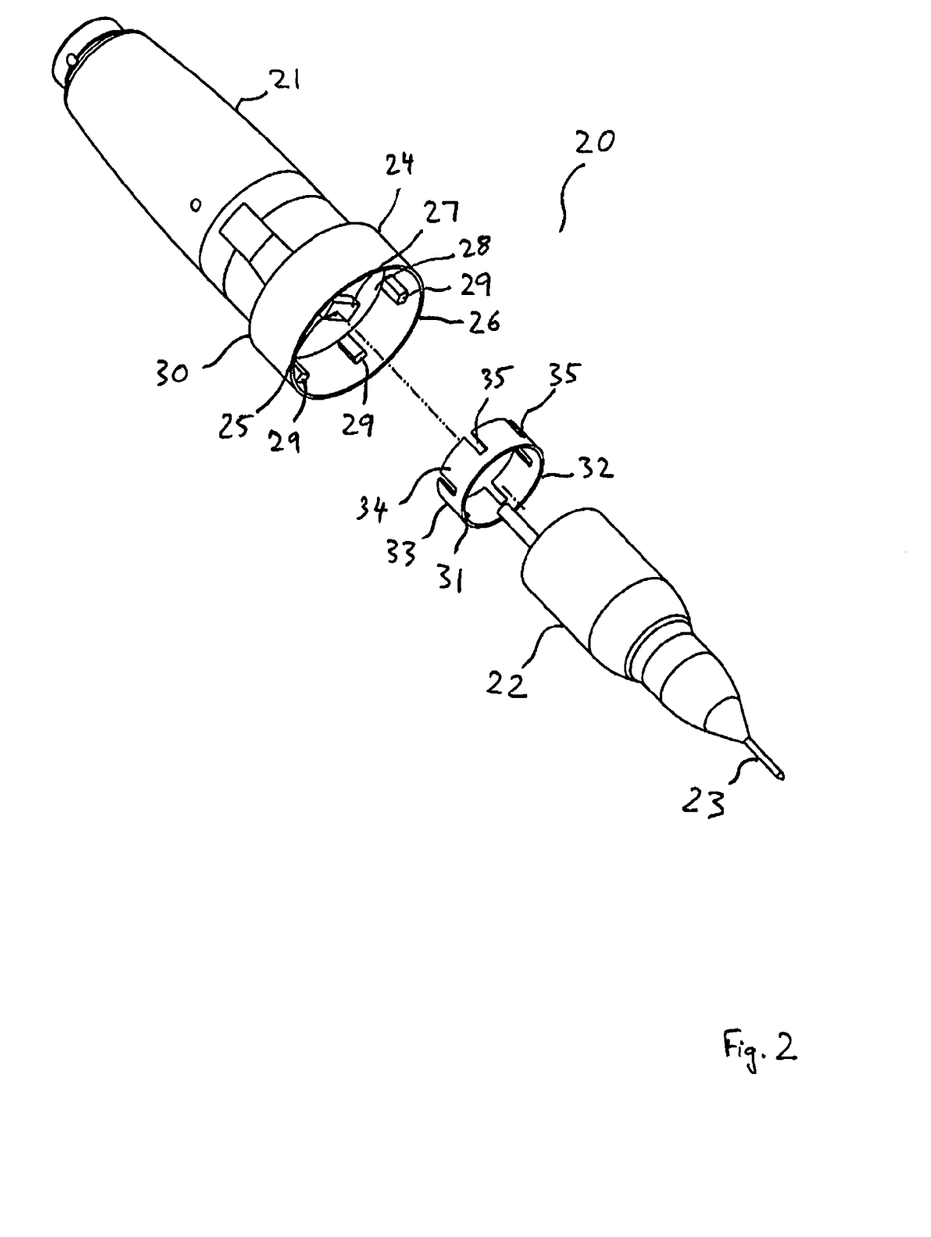
FIG. 2 schematically, a hand-held device.

FIG. 2 shows a hand-held device 20 with a drive module 21 and a needle module 22. A needle 23 is located in the needle module 22. The needle 23 forms a piercing apparatus for piercing the skin which, in other embodiments, can be formed by a system containing several needles.

In the drive module 21 there is an evaluation apparatus 24 with a transmission device 25 and a detection device 26. The transmission device 25 is executed as a light source 27, in particular a light-emitting diode. For example, the transmission device 25 can also be a laser. The light source 27 is arranged in an essentially central position on a surface 28 of the drive module 21 facing the needle module 22. The detection device 26 comprises several light sensors 29 which are arranged on an inner surface of a sensor ring 30. The sensor ring 30 runs around the surface 28 of the drive module 21 facing the needle module 22.

An identification means or mechanism 31 is formed at the needle module 22. The identification means or mechanism 31 comprises a masking means or mechanism 32 for the purpose of masking the light signals discharged from the light source 27. In this embodiment the masking means or mechanism 32 is formed as a mask 33 with a cylinder 34 which has recesses 35.

If the needle module 22 and the drive module 21 are coupled together, the cylinder 34 is arranged in an inner zone of the sensor ring 30. The light source 27 is then arranged in an essentially central position in the mask 33. The cylinder 34 blocks the light signals and the recesses 35 allow the light signals to pass through to the light sensors 29. In this way, the mask 33 masks the light signals sent out from the light source 27. For example, the number and/or the location of the recesses 35 can correspond to an information allocated to the needle module 22. The information can, for example, comprise the serial number or allowed operating parameters such as piercing frequency and operating modes. In this way, the light sensors 29 detect an equal number of light signals as the number of excesses 35. Subsequently, a situation is obtained where the information is transmitted to the drive module 21.

Figure 3A:
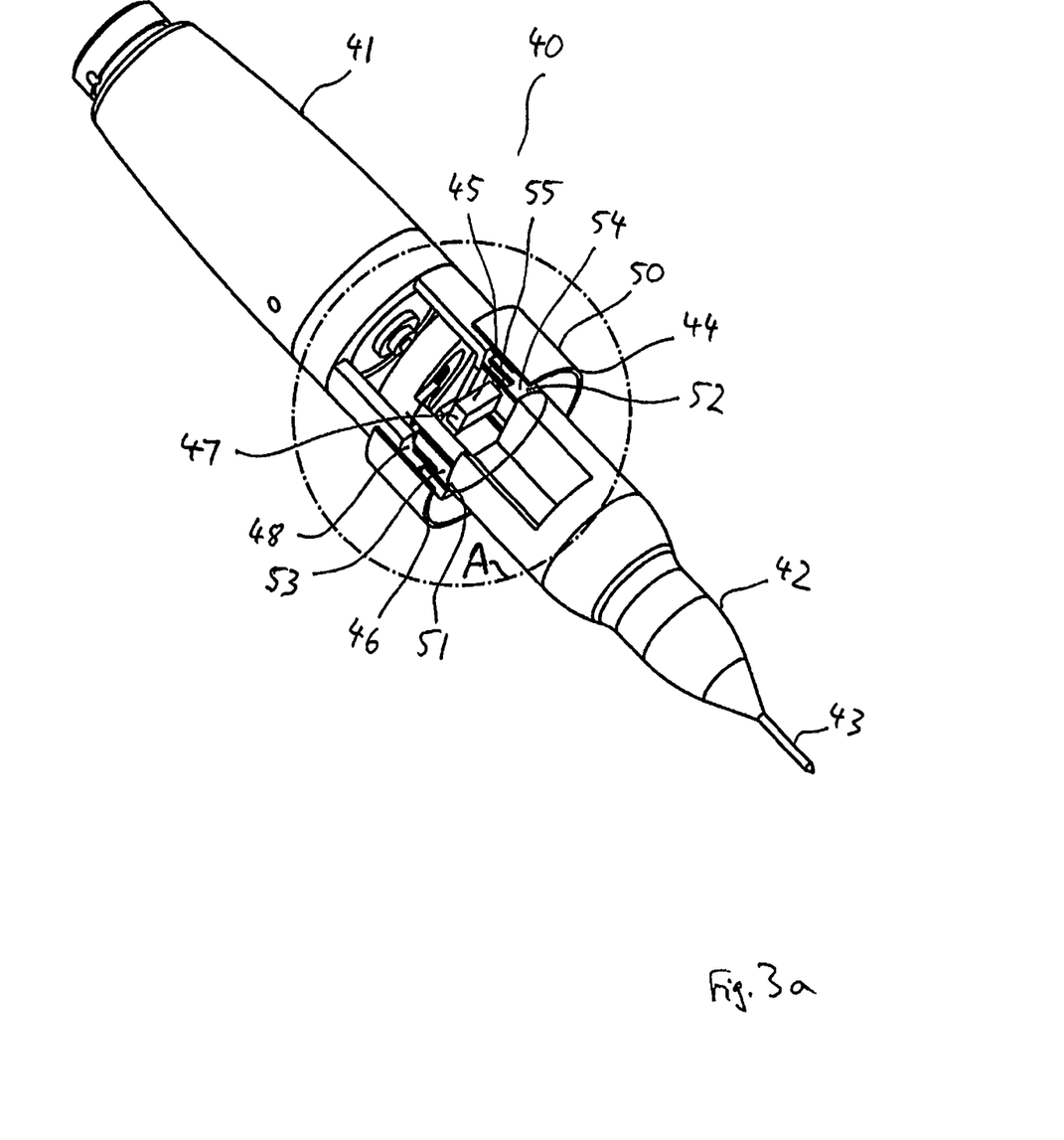
FIG. 3a schematically, a hand-held device in the layout in FIG. 2, wherein the needle module and the drive module are coupled to one another.

FIG. 3a shows schematically a hand-held device 40 with a drive module 41 and a needle module 42 in the embodiment in FIG. 2 that is coupled to the drive module 41. A needle 43 is formed on the needle module 42. At the drive module 41 an evaluation apparatus 44 is formed which comprises a transmission device 45 and a detection device 46. The transmission device 45 is executed as a light source 47, wherein the light source 47 is arranged on a surface 48 of the drive module 41 facing the needle module 42. The detection device 46 comprises light sensors (not shown) which are arranged on an inner surface of a sensor ring 50. The sensor ring 50 runs around the surface 48 facing the needle module 42.

An identification means or mechanism 51 is formed at the needle module 42, wherein the identification means or mechanism 51 has masking means or mechanism 52 for the purpose of masking the light signals discharged from the light source 47. The masking means or mechanism 52 is formed as a mask 53 with a cylinder 54 which has recesses 55. In the same way as the mask 33 in FIG. 2, the mask 53 masks the light signals sent out from the light source 57.

Figure 3B:
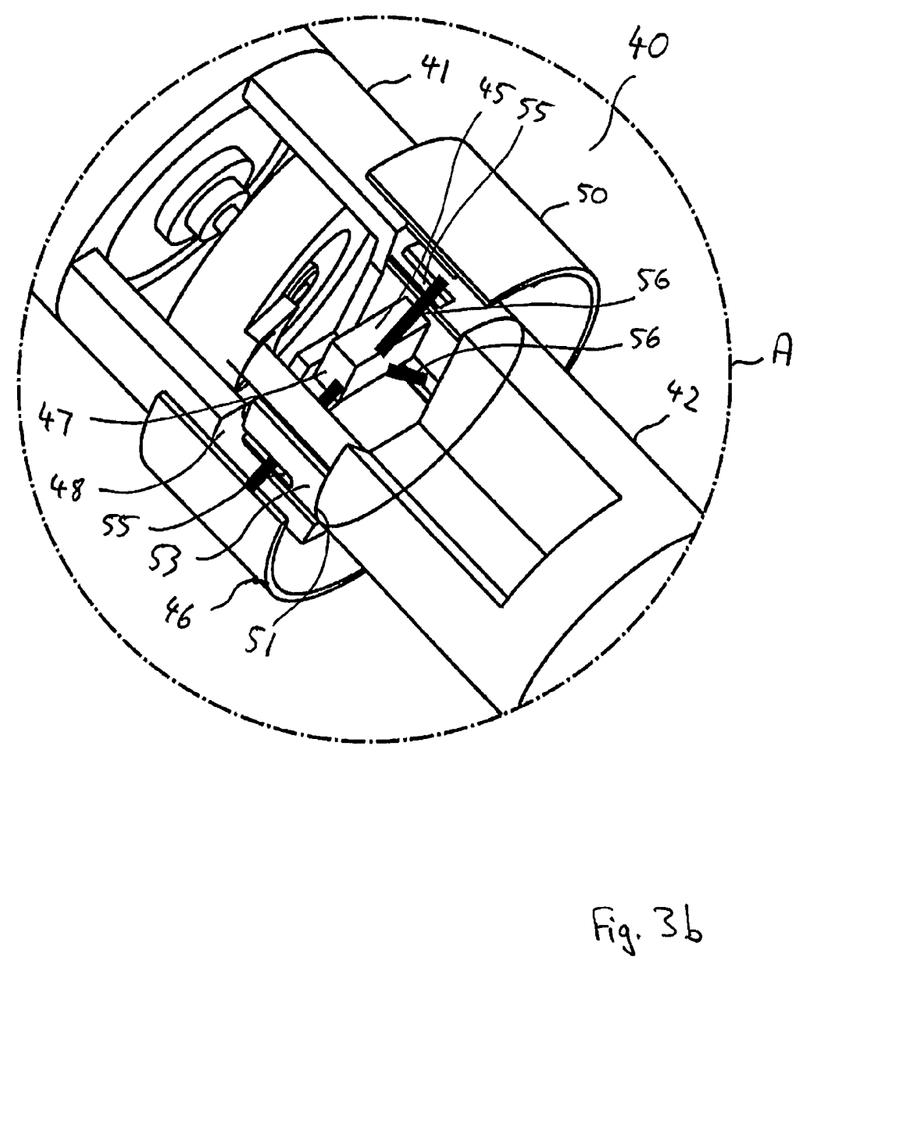

FIG. 3b shows schematically an enlarged partial view of the section from FIG. 3a designated as "A". In FIG. 3b, the same reference numbers as in FIG. 3a are used for similar elements. Furthermore, FIG. 3b shows additional light paths 56 for the light signals sent from the light source 47. It can be clearly seen that the recesses 55 allow the light signals to pass through to the light sensors.

Figure 4A:
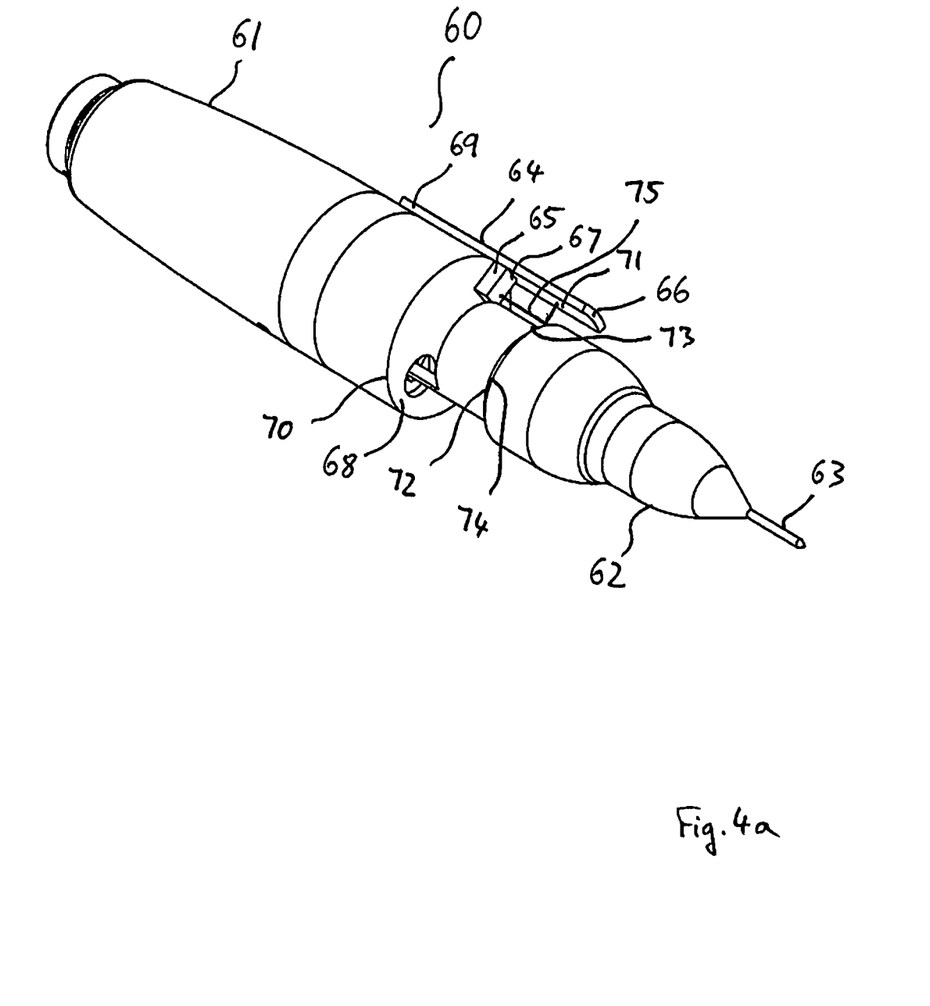
FIG. 4a schematically, a further hand-held device.
Figure 4B:
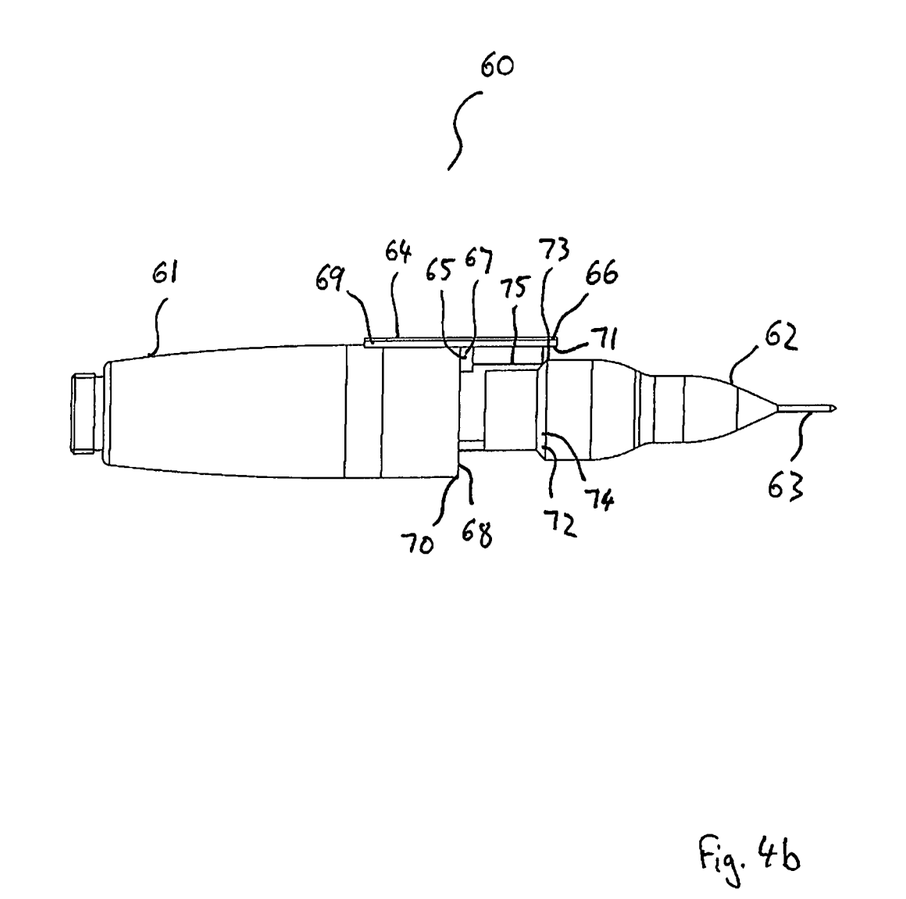
FIG. 4b schematically, the further hand-held device from FIG. 4a in a side view.
Figure 4C:
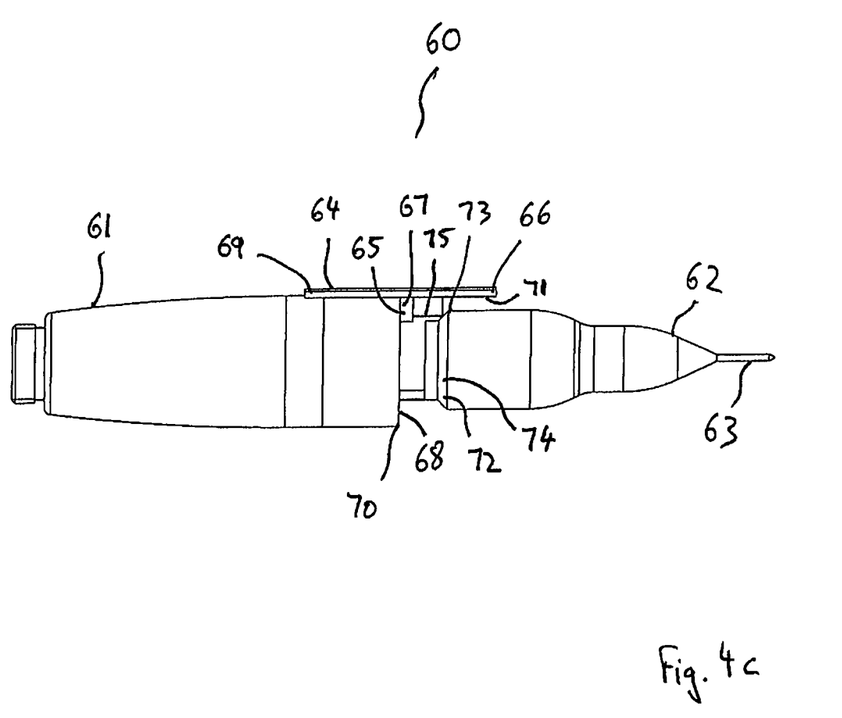
FIG. 4c schematically, the further hand-held device from FIG. 4a, but with another needle module than that in FIG. 4b.

Each of the FIGS. 4a, 4b and 4c show schematically a hand-held device 60 with a drive module 61 and a needle module 62. A needle 63 is located in the needle module 62.

An evaluation apparatus 64 is formed at the drive module 61. The evaluation apparatus 64 comprises a transmission device 65 and a detection device 66. The transmission device 65 is executed as a light source 67. The light source 67 is arranged in an outer area of a surface 68 facing the needle module 62. The detection device 66 is formed on a carrier component 69, wherein the carrier component 69 is arranged extending in the direction of the needle module 62 over the drive module 61 at the drive module 61. In a preferred manner, the light source 67 can be arranged in contact with the carrier component 69 on the surface 68 facing the needle module 62 in order to additionally support the carrier component 69. On the carrier component 69 several light sensors are arranged on a side facing the surface 68, through which a light sensor row 71 is formed.

An identification means or mechanism is formed at the needle module 62. The identification means or mechanism comprises a signal conducting means or mechanism 73 for the purpose of conducting the light signals 75 sent out from the light source 67. The signal conducting means 73 are formed as a reflecting surface 74. The reflecting surface 74 is arranged at an angle with reference to a longitudinal axis of the hand-held device 60 at the needle module 62, so that the light signals 75 are reflected onto the sensor row 71 if the needle module 62 is coupled to the drive module 61.

The reflecting surface 74 in the FIG. 4b is arranged in another area of the needle module 62 than the reflecting surface 74 in the FIG. 4c. In this way the situation is obtained where the light signals 74 are reflected onto different areas of the sensor row 71 if the drive module 61 is coupled to the needle module 61. For example, an information can be allocated to a positioning of the reflecting surface 74 on the needle module 62. The information can comprise, for example, a serial number or an operating mode of the needle module 62. The detection device 66 detects the corresponding position of the reflected light signals 74 from the surface 74 onto the sensor row 71, through which the information is transmitted to the drive module 61.

Figure 5A:
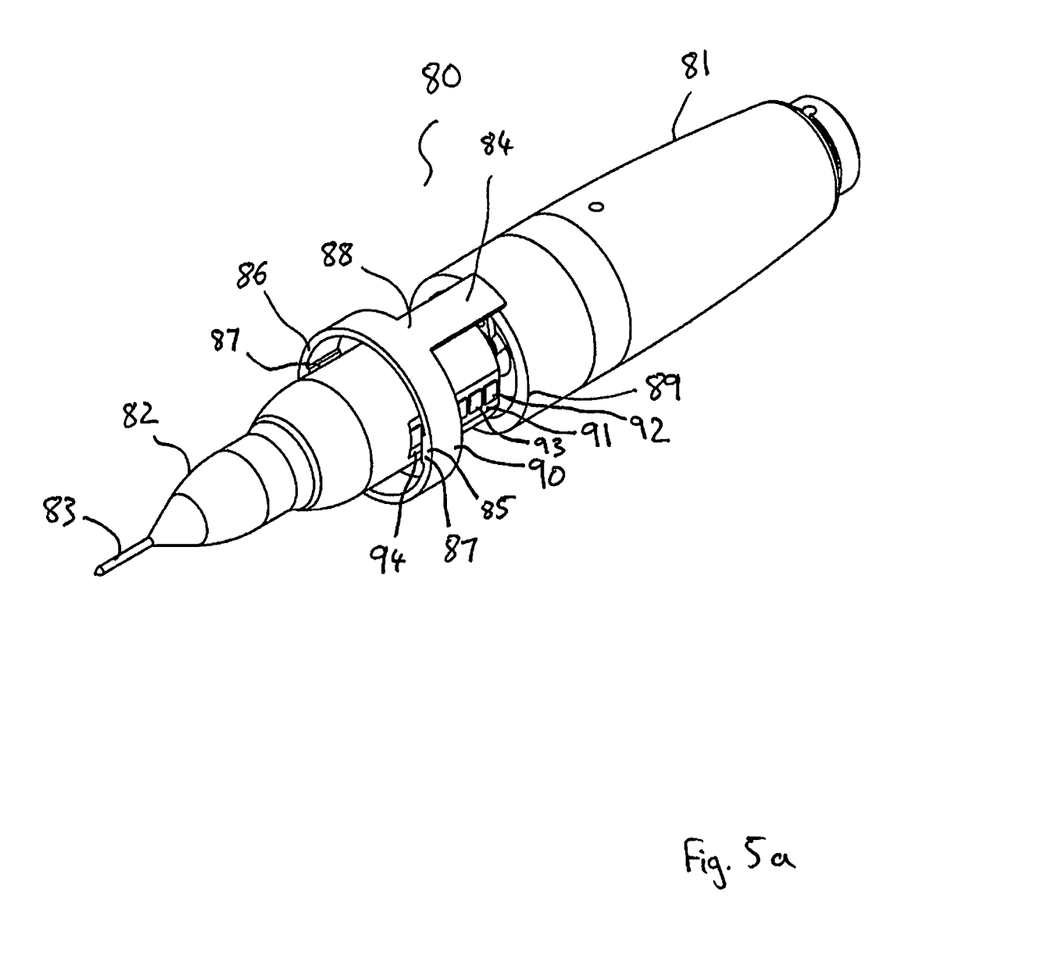
FIG. 5a schematically, another hand-held device.
Figure 5B:
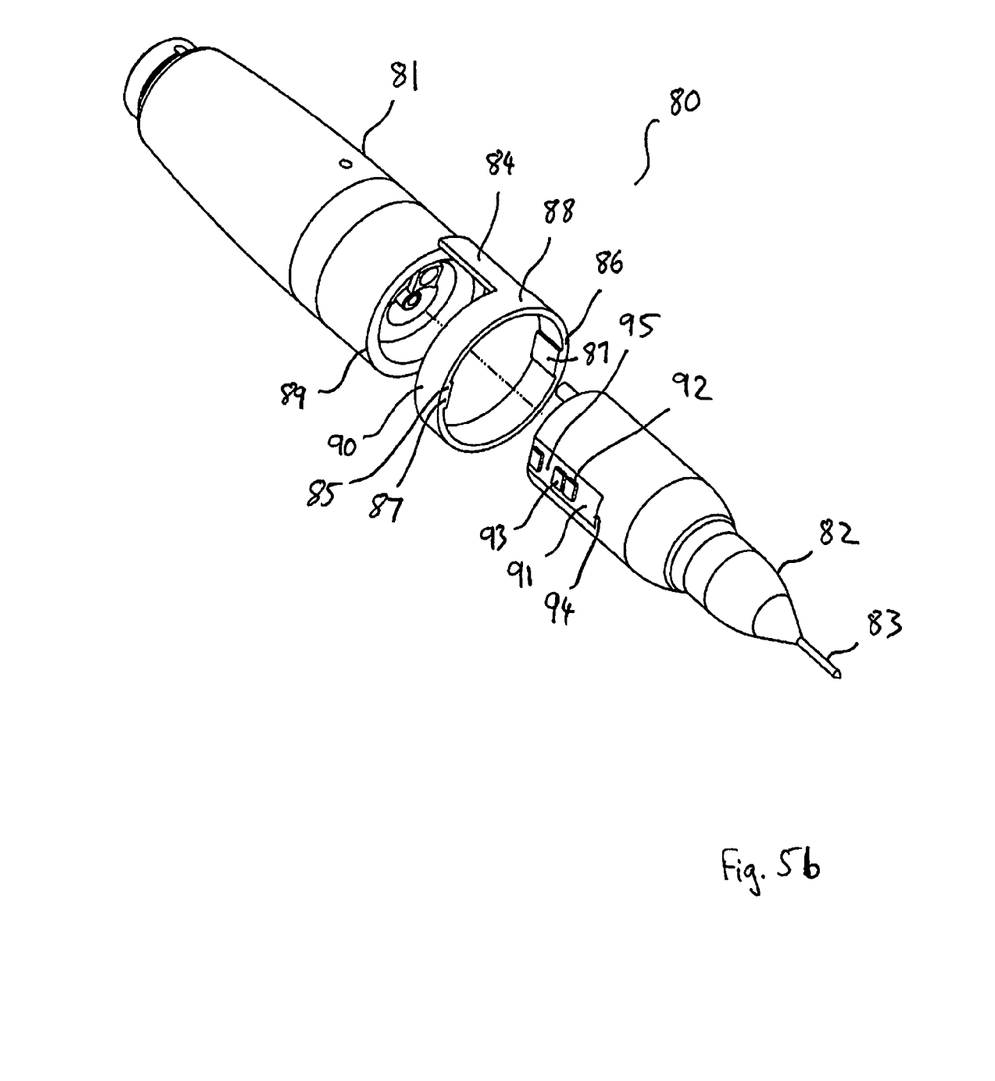
FIG. 5b schematically, the hand-held device from FIG. 5a in another view.
Figure 5C:
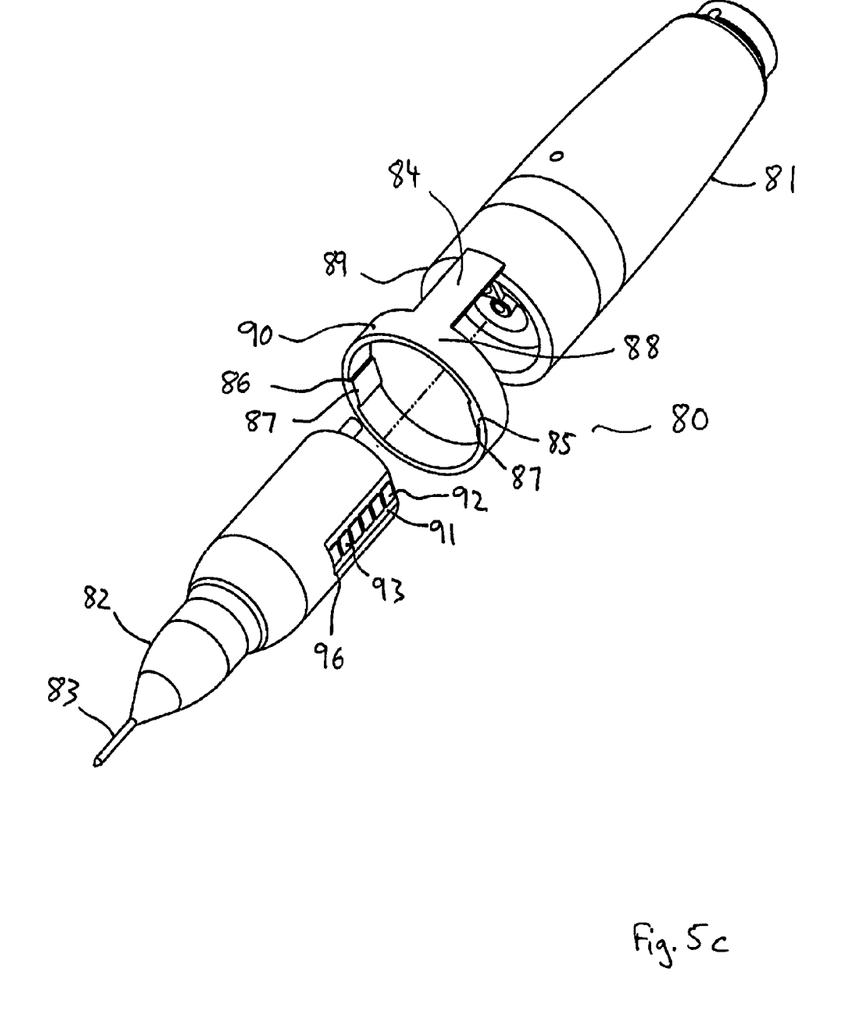
FIG. 5c schematically, the hand-held device from FIG. 5a in a further view.

Each of the FIGS. 5a, 5b and 5c shows schematically a hand-held device 80 with a drive module 81 and a needle module 82. A needle 83 is arranged in the needle module 82.

An evaluation apparatus 84 is arranged at the drive module 81. The evaluation apparatus 84 comprises a transmission device 85 and a detection device 86. The transmission device 85 comprises several light sources (not shown). The detection device 86 comprises several sensors (not shown). The multiplicity of light sources and the multiplicity of sensors are located adjacent to one another in several areas 87. The multiplicity of areas 87 is formed at a carrier component 88, wherein the carrier component 88 is arranged extending over an end 89 of the drive module 81, facing the needle module 82, at the drive module 81. The carrier component 88 has a ring form at an end facing away from the drive module 81, wherein the multiplicity of areas 87 is arranged on an inner surface of the ring form, through which a sensor ring 90 is formed.

An identification means or mechanism 91 is formed at the needle module 82. The identification means or mechanism 91 comprises a signal conducting means or mechanism 92 for the purpose of conducting the light signals discharged from the several light sources. The signal conducting means or mechanism 92 is formed as reflecting elements 93. The reflecting elements 93 are arranged in a recognition zone 94 adjacent to one another. It can be envisaged that a non-reflecting area 95, as shown in FIG. 5b, is formed between two reflecting elements 93.

If the needle module 82 and the drive module 81 are coupled to one another, then the transmission device 85 wipes over the recognition zone 94 and the light signals are reflected by the reflecting elements 93 and detected by the multiplicity of sensors. For example, an information allocated to the needle module 82 can be allocated to the number of the reflecting elements 93. The information is transferred to the drive module 81 wherein the number of the reflected light signals is detected by the sensors. For example, a detected reflected light signal can correspond to the binary One. The binary Zero corresponds then to the case where no reflected light signal is detected, meaning, if the multiplicity of light sources wipes over the non-reflecting area 95 in the recognition zone 94.

FIG. 5c shows additionally to the recognition zone (not shown) yet another reference area 96 formed at the needle module 82. The reference area 96 comprises reflecting elements 93 arranged adjacent to one another. In another embodiment, non-reflecting areas can also be formed between the reflecting elements 93. For example, the number of the reflecting elements 93 and/or the non-reflecting areas 95 can be known, through which an allocation of the detected and reflected light signals to the binary One is made possible in a simplified manner.

The features of the invention as disclosed in this description, in the claims and in the drawings can be of significance both individually as well as in random combination for the realisation of the invention in its various embodiments.

The invention claimed is:

1. A hand-held device for the repeated piercing of a skin, the hand-held device has
a drive module with an evaluation apparatus and a drive unit that is configured for the purpose of producing a driving force, and
a needle module in which a piercing apparatus is moveably located in the longitudinal direction of the needle module and which is detachably coupled to the drive module in such a way that the driving force is conducted into the piercing apparatus, and the needle module comprising an identification mechanism which is allocated to the evaluation apparatus, wherein
the evaluation apparatus comprising an optical transmission device with a light source emitting optical signals, the identification mechanism comprising a mask configured for masking the optical signals emitted by the light source according to a code allocated to the needle module; and the evaluation apparatus comprising an optical detection device for detecting the masked optical signals.

2. The device according to claim 1, wherein the identification mechanism can be evaluated by the evaluation apparatus with the support of at least one of the following evaluation methods: wireless data transmission including radio data transmission, infrared data transmission and bluetooth data transmission, inductive evaluation, capacitive evaluation, optical evaluation and mechanical evaluation.

3. The device according to claim 1, wherein the mask has a signal conducting mechanism which is configured for the purpose of sending the optical signals discharged from the light source toward the evaluation apparatus.

4. The device according to claim 1, wherein the identification mechanism have an electronic identification mechanism with data stored therein which can be evaluated by the evaluation apparatus.

5. The device according to claim 4, wherein the evaluation apparatus comprises a communication module allocated to the electronic identification mechanism with which the stored data can be read out of the electronic identification mechanism and, further data can be stored in the electronic identification mechanism.

6. The device according to claim 4, wherein the electronic identification mechanism comprises an RFID-chip.

7. The device according to claim 1, wherein the evaluation apparatus is configured for the purpose of automatically evaluating the identification mechanism if the needle module is coupled to the drive module.

8. The device according to claim 1, wherein the identification mechanism is formed to supply at least one of the following information items that can be evaluated by the evaluation apparatus and that can be allocated to the needle module: serial number, for the drive module usable for the needle module, usage duration of the needle module, type of piercing apparatus and allowed operating parameters including piercing frequency and operating modes.

9. The device according to claim 1, further comprising a control device configured to control an operation of the hand-held device.

10. The device according to claim 9, wherein the control device is disposed in at least one of the following equipment components: the hand-held device and a control unit coupled to the hand-held device.

11. The device according to claim 9, wherein the evaluation apparatus or the control device are configured for the purpose of blocking the operation of the hand-held device if it is discovered during the evaluation of the identification mechanism that the needle module is not authorised for usage with the drive module.

12. The device according to claim 9, wherein at least one of the evaluation apparatus and the control device are configured for the purpose of controlling the operation of the hand-held device according to at least one information item that can be evaluated by the evaluation apparatus and that is allocated to the needle module.

13. The device according to claim 1, wherein the hand-held device is executed as one of the following hand-held devices: permanent make-up and tattoo hand-held device, hand-held device for discharging active ingredients, and skin vaccination hand-held device.

14. The device according to claim 1, wherein the needle module is a sterilised and disposable needle module.

15. A needle module having a needle module casing which has a coupling mechanism for allowing a detachable coupling of the needle module casing to a drive module of a drive unit of a hand-held device, and the needle module further including a piercing apparatus which is moveably arranged in the longitudinal direction in the needle module casing and an identification mechanism comprising a mask capable of masking optical signals according to a code allocated to the needle module.

16. A method for assembling of a hand-held device with which a skin can be pierced, the method comprising the steps of: providing the hand-held device including a drive module with an evaluation apparatus and a drive unit which is configured for the purpose of producing a driving force, arranging a needle module in which a piercing apparatus is moveably arranged in the longitudinal direction of the needle module, and detachably coupling the needle module so that the driving force can be routed into the piercing apparatus, and providing an identification mechanism which is allocated to the evaluation apparatus and configuring the evaluation apparatus for evaluating the identification mechanism by using an optical transmission device with a light source emitting optical signals, providing the identification mechanism with a mask configured for masking the optical signals emitted by the light source according to a code allocated to the needle module, and providing an optical detection device for detecting the optical signals following the step of masking.

17. The method according to claim 16, wherein the step of evaluation the identification mechanism is accomplished with the support of at least one of the following evaluation methods by the evaluation apparatus: wireless data transmission including radio data transmission, infrared data transmission and bluetooth data transmission, inductive evaluation, capacitive evaluation and mechanical evaluation.

18. The method according to claim 16, further comprising the step of providing the mask with a signal guiding mechanism so that the optical signals are discharged from the light source and guided toward the evaluation apparatus.

19. The method according to claim 16, further comprising the step of providing the identification mechanism with an electronic identification mechanism with data stored therein which are evaluated by the evaluation apparatus.

20. The method according to claim 19, further comprising the steps of providing the evaluation apparatus with a communication module allocated to the electronic identification mechanism, with which and during the evaluation of the electronic identification mechanism, reading out the stored data at least partially from the electronic identification mechanism and, storing further data in the electronic identification mechanism.

21. The method according to claim 19, wherein the evaluating step of the electronic identification mechanism includes evaluating data are evaluated from an RFID-chip comprised by the electronic identification mechanism.

22. The method according to claim 16, wherein the evaluating step of the evaluation apparatus includes automatically evaluating the identification mechanism to see if the needle module is coupled to the drive module.

23. The method according to claim 16, further comprising providing the identification mechanism with at least one of the following information items that can be evaluated in the evaluation step by the evaluation apparatus and that can be allocated to the needle module: serial number, for the drive module usable for the needle module, usage duration of the needle module, type of piercing apparatus and allowed operating parameters including piercing frequency and operating modes.

24. The method according to claim 16, further comprising the steps of providing a control device and through at least one of the evaluation apparatus and the control device, blocking operation of the hand-held device if it is discovered during the evaluating step of the identification mechanism that the needle module is not authorised for usage with the drive module.

25. The method according to claim 24, further comprising the steps of controlling at least one of the evaluation apparatus and the control device according to information in the evaluating step by the evaluation apparatus and that can be allocated to the needle module.

\* \* \* \* \*